US011330968B2

(12) United States Patent
Beyer et al.

(10) Patent No.: US 11,330,968 B2
(45) Date of Patent: May 17, 2022

(54) STERILE ENDOSCOPE SHEATH

(71) Applicant: avateramedical GmbH, Jena (DE)

(72) Inventors: Stefan Beyer, Berlin (DE); Fabian Weise, Berlin (DE)

(73) Assignee: avateramedical GmbH

( * ) Notice: Subject to any disclaimer, the term of this patent is extended or adjusted under 35 U.S.C. 154(b) by 186 days.

(21) Appl. No.: 16/395,504

(22) Filed: Apr. 26, 2019

(65) Prior Publication Data

US 2019/0328216 A1  Oct. 31, 2019

(30) Foreign Application Priority Data

Apr. 26, 2018 (DE) .......................... 102018110082.5

(51) Int. Cl.
*A61B 1/00* (2006.01)
*A61B 1/05* (2006.01)
*A61B 1/06* (2006.01)

(52) U.S. Cl.
CPC ...... *A61B 1/00142* (2013.01); *A61B 1/00096* (2013.01); *A61B 1/00163* (2013.01); *A61B 1/05* (2013.01); *A61B 1/0653* (2013.01)

(58) Field of Classification Search
CPC ............ A61B 1/00096; A61B 1/00135; A61B 1/00142; A61B 1/00165; A61B 1/042; A61B 1/0669; A61B 1/07; A61B 1/00057; A61B 1/00172; A61B 1/05; A61B 1/051; A61B 1/053; A61B 1/0638; H04N 5/343
See application file for complete search history.

(56) References Cited

U.S. PATENT DOCUMENTS

| 5,257,617 | A | | 11/1993 | Takahashi | |
|---|---|---|---|---|---|
| 5,370,649 | A | * | 12/1994 | Gardetto | A61B 18/24 606/15 |
| 5,785,643 | A | | 7/1998 | Lynn | |
| 6,122,042 | A | * | 9/2000 | Wunderman | A61B 1/05 356/343 |
| 6,447,444 | B1 | * | 9/2002 | Avni | A61B 1/31 600/121 |

(Continued)

FOREIGN PATENT DOCUMENTS

| DE | 3433889 A1 | 6/1988 |
|---|---|---|
| DE | 102010022429 A1 | 12/2011 |

(Continued)

OTHER PUBLICATIONS

Machine Translation of Office Action and search report from corresponding European application No. 19169706.9, dated Aug. 21, 2019.

*Primary Examiner* — Michael J Carey
*Assistant Examiner* — Stephen Floyd London
(74) *Attorney, Agent, or Firm* — McGarry Bair PC

(57) ABSTRACT

An arrangement for sterile handling of a non-sterile endoscope in a sterile environment includes a sterile endoscope sheath having an optical element arranged at its distal end, and a non-sterile endoscope. The optical element has a light-reflecting element or a light-reflecting area which reflects detection light emitted by the detection light source as reflection light toward a proximal end of the endoscope sheath. The non-sterile endoscope includes an endoscope shaft, an illumination optical system, and an observation optical system. The non-sterile endoscope is received in the endoscope sheath.

8 Claims, 8 Drawing Sheets

(56) References Cited

U.S. PATENT DOCUMENTS

| | | | |
|---|---|---|---|
| 6,503,196 B1 * | 1/2003 | Kehr | A61B 1/00096 600/129 |
| 10,588,490 B2 | 3/2020 | Friedrich | |
| 2002/0103420 A1 * | 8/2002 | Coleman | A61B 1/00087 600/173 |
| 2002/0115908 A1 * | 8/2002 | Farkas | G02B 23/2438 600/178 |
| 2002/0139920 A1 * | 10/2002 | Seibel | A61B 1/00172 250/208.1 |
| 2005/0159646 A1 | 7/2005 | Nordstrom | |
| 2006/0173242 A1 * | 8/2006 | Navok | A61B 1/07 600/133 |
| 2006/0276692 A1 * | 12/2006 | Kucklick | A61B 1/012 600/175 |
| 2008/0064925 A1 * | 3/2008 | Gill | A61B 1/00142 600/109 |
| 2014/0107496 A1 * | 4/2014 | Hellstrom | A61B 1/05 600/478 |
| 2014/0200406 A1 * | 7/2014 | Bennett | A61B 1/0646 600/109 |
| 2014/0288365 A1 * | 9/2014 | Henley | A61B 1/00036 600/103 |
| 2015/0010878 A1 * | 1/2015 | Seibel | G01J 3/0218 433/27 |
| 2015/0374208 A1 * | 12/2015 | Ruppersberg | A61B 1/05 600/109 |
| 2016/0143519 A1 * | 5/2016 | Harris | A61B 1/00096 600/186 |

FOREIGN PATENT DOCUMENTS

| | | | |
|---|---|---|---|
| DE | 102010053814 A1 | 6/2012 | |
| DE | 102016007669 A1 * | 12/2017 | A61B 1/07 |
| DE | 102016007669 A1 | 12/2017 | |
| EP | 0520743 A1 | 12/1992 | |
| EP | 0904725 A1 | 3/1999 | |
| EP | 0820250 B1 * | 9/2003 | G02B 13/22 |
| EP | 0820250 B1 | 9/2003 | |
| WO | 00-59366 A2 | 10/2000 | |

\* cited by examiner

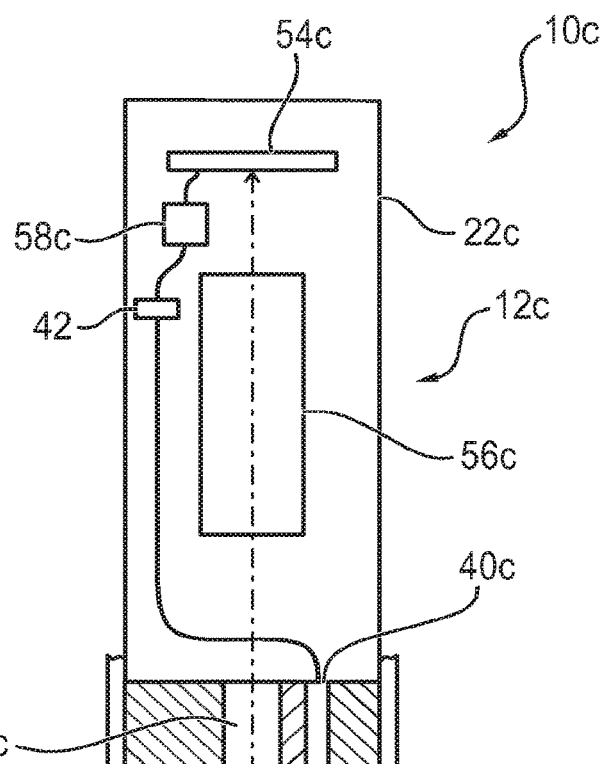
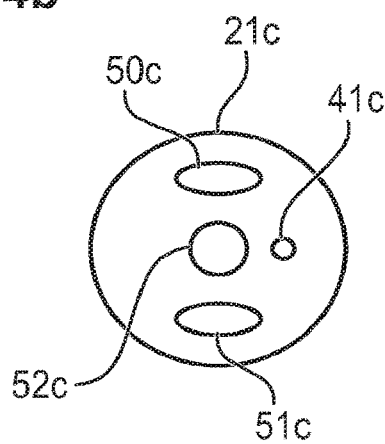
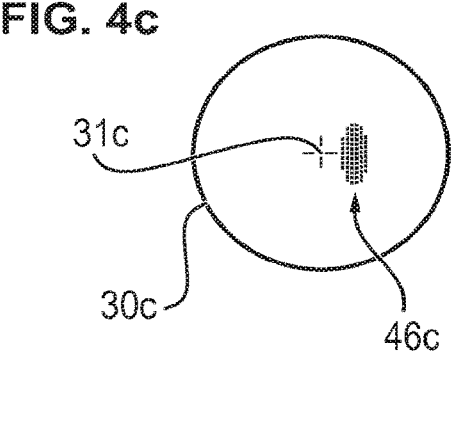
FIG. 4a
FIG. 4b
FIG. 4c

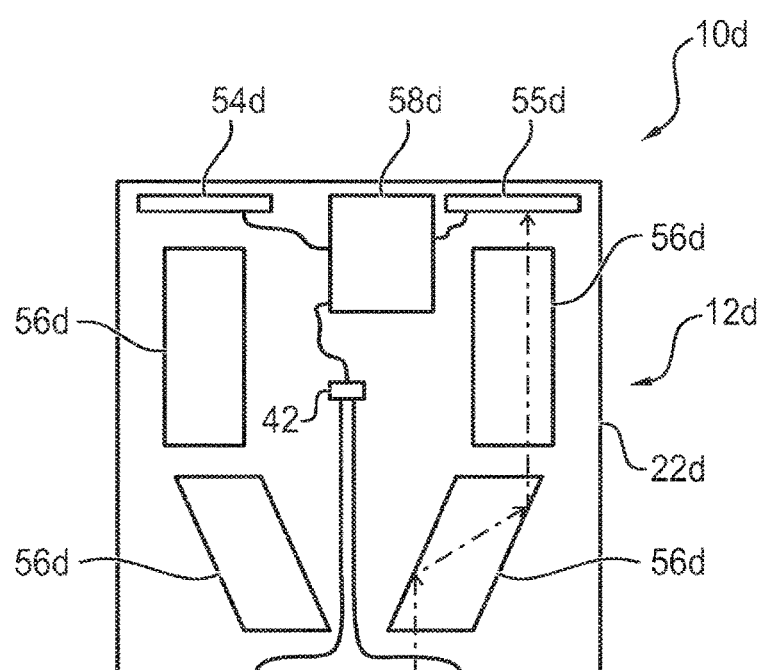
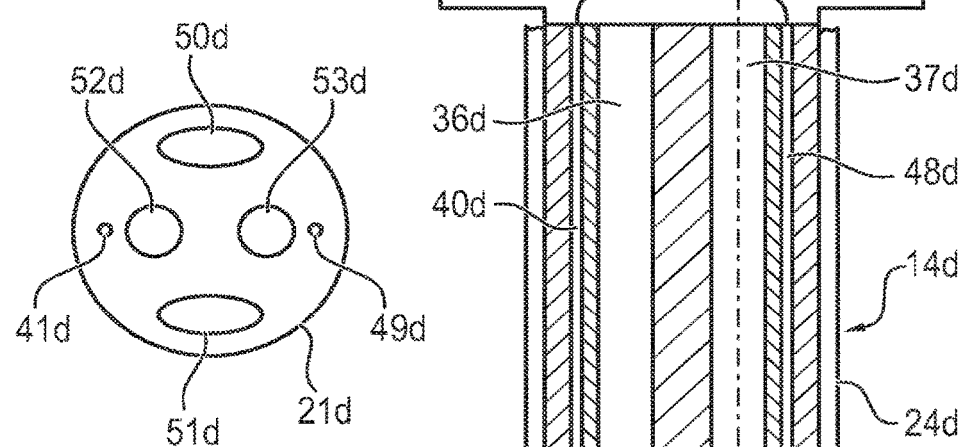
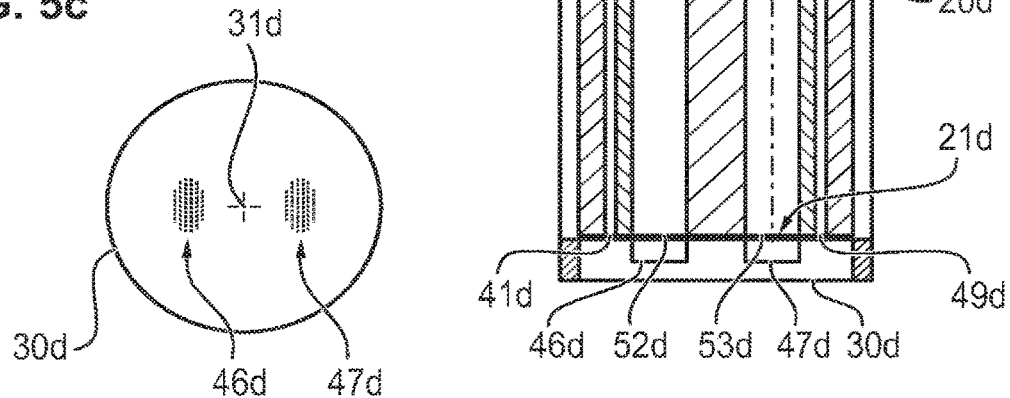

FIG. 6a
FIG. 6b
FIG. 6c
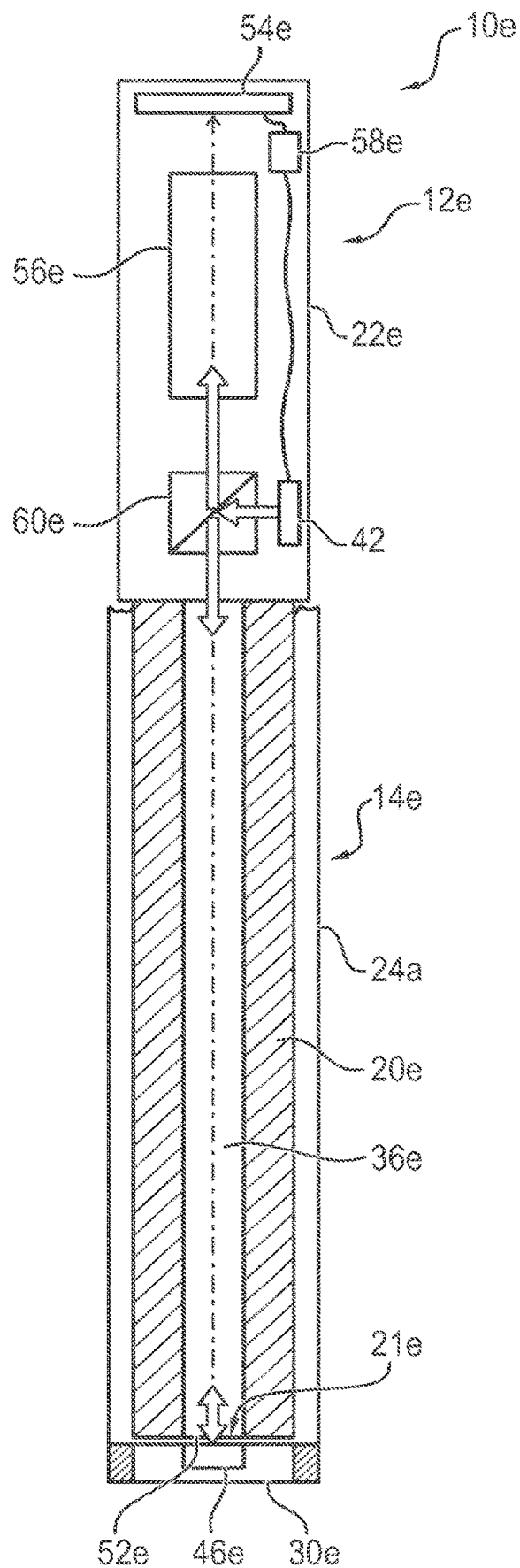
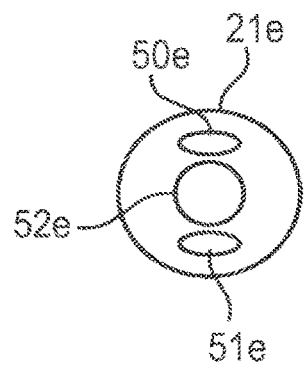
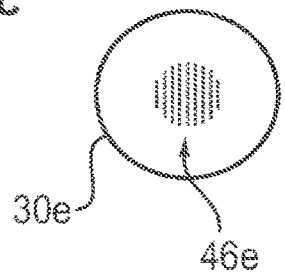

STERILE ENDOSCOPE SHEATH

CROSS REFERENCE TO RELATED APPLICATION

This application claims the benefit of German Application DE 10 2018 110 082.5, filed on Apr. 26, 2018, which is incorporated herein in its entirety.

BACKGROUND

The invention relates to a sterile endoscope sheath for a non-sterile endoscope. The endoscope sheath comprises an optical element arranged at a distal end of the endoscope sheath, i.e. an end facing a patient. Further, the invention relates to an arrangement for the sterile handling of a non-sterile endoscope in a sterile environment.

Known arrangements for the sterile handling of a non-sterile endoscope in a sterile environment, such as an operating room, comprise a non-sterile endoscope and a sterile endoscope sheath, such an endoscope sheath also being referred to as "drape". The endoscope sheath is typically a sterile disposable article or an endoscope sheath which can again be sterilized, i.e. reprocessed. Such an endoscope sheath is, for example, known from document DE 10 2010 022 429 A1. The endoscope sheath has two sheath parts which are mechanically connected to each other in a releasable and fluid-tight manner. Further, document DE 10 2010 053 814 A1 discloses an endoscope for medical purposes, which can be inserted into a sterilized housing.

The disadvantage of endoscope sheaths known up to now is that it cannot be guaranteed whether the endoscope is correctly inserted into the endoscope sheath and whether an optical element arranged at the distal end of the endoscope sheath, for example an exit window, both sits correctly and has not been damaged. If an endoscope which has not correctly been inserted into an endoscope sheath is used for imaging in the case of a patient, problems in the imaging or transmission may occur, as a result whereof considerable risks for the health of the patient may arise.

From document EP 0 904 725 A1, an endoscope having a replaceable shaft is known, which is formed as a sterile disposable article. The disadvantages of this endoscope are the comparably high costs incurred by the replacement of the shaft with every use.

From document US 2014/0200406 A1, an endoscope is known, in which the fogging of a distally arranged optical element, i.e. arranged on a side facing a patient, is prevented by means of infrared light. From document US 2014/0200406 A1, further a method is known in which with the aid of the infrared light the presence of the optical element is checked.

Document DE 34 33 889 A1 discloses an optical arrangement for object recognition, with an endoscope and a retroreflector.

Further, from document EP 0 820 250 B1, a system for the endoscopic diagnosis is known which uses both visible and infrared light for imaging.

SUMMARY OF THE INVENTION

Starting from the known prior art, it is the object of the invention to specify an endoscope sheath, where one can reliably check whether the endoscope sheath is correctly installed. In addition, an arrangement for the sterile handling of a non-sterile endoscope in a sterile environment is to be specified.

This object is solved by an endoscope sheath having an optical element arranged at a distal end of the endoscope sheath, wherein the optical element has one of a light-reflecting element or a light-reflecting area which reflects detection light emitted from a detection light source as reflection light toward a proximal end of the endoscope, and by an arrangement having a sterile endoscope sheath having an optical element arranged at a distal end of the endoscope sheath wherein the optical element has one of a light-reflecting element or a light-reflecting area which reflects detection light emitted from a detection light source as reflection light toward a proximal end of the sterile endoscope sheath, and a non-sterile endoscope comprising an endoscope shaft, an illumination optical system for guiding illumination light and an observation optical system for one of detecting or forwarding ambient light entering a distal end of the endoscope shaft, wherein the non-sterile endoscope is received in the endoscope sheath and is shielded by it in a sterile manner against the environment. Advantageous developments are specified in the dependent claims.

The inventive endoscope sheath comprises an optical element arranged at a distal end of the endoscope sheath. The optical element has a light-reflecting element or a light-reflecting area which reflects detection light emitted from a detection light source as reflection light toward a proximal end of the endoscope sheath. In the simplest case, the optical element is formed as a transparent element not shaping the light. This can be a simple window. Alternatively, the optical element may be formed as a lens or a prism. The light-reflecting element may, for example, be applied to or glued on the optical element or mechanically connected to the optical element. Alternatively, the optical element and the light-reflecting element are integrally formed as one piece. The light-reflecting area can, for example, be formed by cutting the optical element or by a surface treatment, such as vapor-coating with a metal (metallizing) or vapor deposition of dielectric films. Preferably, the light-reflecting element or the light-reflecting area is a light-reflecting coating which is applied to the optical element. As a result, a safe and cost-efficient monitoring of the correct arrangement of the endoscope in the endoscope sheath and the correct arrangement of the optical element, for example, an exit window, on the endoscope sheath is possible.

In this document, distal refers to a direction facing the patient and proximal refers to a direction facing away from the patient. When referring to an element, an object or an arrangement, distal and proximal are used in relation to the intended position of the element, the object and the arrangement, respectively.

Since the detection light is reflected on the optical element, the presence of the optical element and thus the presence of the sterile endoscope sheath can be determined reliably by way of detection of the reflection light. As a result, it may also be prevented that a non-sterile endoscope is inserted into the patient without the sterile endoscope sheath. Further, by determining optical characteristics of the reflection light, such as the light intensity, conclusions on the position of the optical element may be drawn. This makes it possible, on the one hand, to reliably determine the correct installation of the endoscope sheath. On the other hand, it makes it possible to determine production errors or transport damages. For example, an incorrect arrangement of the endoscope in the sheath may be determined when the optical element has come off or the endoscope sheath has gone out of shape during transport. When a continuous detection of the reflection light takes place, damages in use, for example when cleaning during a surgery, may be determined.

By the light-reflecting element or the light-reflecting area a cost-efficient solution is created, with which it can reliably be checked whether the endoscope sheath is correctly installed or whether the endoscope is correctly positioned in the endoscope sheath. In particular, the correct seat of the endoscope sheath on the endoscope can be determined. In addition, the light-reflecting element or the light-reflecting area does not result in a problem when keeping regulatory demands, such as rules of hygiene as well as rules relating to the electrical safety or temperature distribution.

It is advantageous when the light-reflecting element or the light-reflecting area is transparent in at least one optical wavelength range outside the wavelength range of the detection light. In particular, the light-reflecting element or the light-reflecting area reflects light in a wavelength range within the wavelength range of the detection light. The optical element is transparent or largely transparent to light in the at least one optical wavelength range. This increases the optical quality of the optical element of the endoscope sheath. Preferably, the light-reflecting element or the light-reflecting area is transparent in a wavelength range of visible light, i.e. in particular from 380 nm to 780 nm. This makes it possible to use the optical element, for example in connection with an endoscope, for imaging in the optical area, without this causing interferences by the light-reflecting element or the light-reflecting area in the imaging.

Further, it is advantageous when the light-reflecting element or the light-reflecting area reflects light in an ultraviolet (UV) wavelength range, i.e. between 280 nm and 380 nm, in an infrared (IR) wavelength range, i.e. between 3 µm and 1 mm, or in a near-infrared (NIR) wavelength range, i.e. between 780 nm and 3 µm. As a result, only light with a wavelength range outside the visible light is used as reflection light. This reduces the influence of ambient light on the detection of the reflection light and thus increases the reliability with which the correct seat of the optical element and thus the correct seat of the endoscope sheath can be determined.

Preferably, the light-reflecting element or the light-reflecting area is arranged on a side of the optical element facing the proximal end of the endoscope sheath. In particular, the light-reflecting element or the light-reflecting area is arranged on a side of the optical element facing the inside of the endoscope sheath. As a result, the light-reflecting element or the light-reflecting area are insensitive to external influences, in particular to contaminations and liquids, which would reduce the capability of the light-reflecting element to reflect the detection light and would thus make a detection of the reflection light more unreliable.

The invention further relates to an arrangement for the sterile handling of a non-sterile endoscope in a sterile environment. The inventive arrangement comprises an inventive sterile endoscope sheath as described herein or according to an advantageous development and a non-sterile endoscope. The endoscope comprises an endoscope shaft, an illumination optical system for guiding illumination light and an observation optical system for detecting and/or forwarding ambient light entering a distal end of the endoscope shaft. The endoscope is received in the endoscope sheath and is shielded by it in a sterile manner against the environment. Preferably, the observation optical system forms at least one optical channel.

The use of the non-sterile endoscope in connection with the sterile endoscope sheath is a cost-efficient alternative to the re-sterilization of endoscopes that can be used multiple times or to the use of disposable endoscopes. Further, the inventive endoscope sheath makes it possible to reliably check whether the endoscope is correctly installed in the endoscope sheath. As a result, it can be prevented that the endoscope is used during a surgery with an incorrectly seated endoscope sheath or completely without the sterile endoscope sheath, which may cause considerable risks for the health of the patient. For example, a trocar may be provided that only provides access to the situs, i.e. to the opened operating area, of the patient when the correct seat of the endoscope sheath has been determined. Thus, the inventive arrangement enables a cost-efficient and safe handling of a non-sterile endoscope in a sterile environment.

It is advantageous when the endoscope has a detection optical system for guiding the detection light emitted by the detection light source, which system is different from the illumination optical system and the observation optical system. For example, the detection light may be guided through an optical fiber, in particular a glass fiber having a thickness, in particular with a core diameter, between 3 µm and 1 mm from the detection light source to the distal end of the endoscope shaft. As a result, the light-reflecting element or the light-reflecting area can safely be illuminated with the detection light so that sufficient reflection light is reflected and thus a reliable detection of the reflection light is guaranteed. Preferably, the light-reflecting element or the light-reflecting area is arranged such that, in the case of the intended use of the arrangement, a distal end of the detection optical system and the light-reflecting element or the light-reflecting area are opposite to each other.

Further, it is advantageous when the observation optical system guides the reflection light. The optical channel formed by the observation optical system can be used to guide the reflection light from the distal end of the endoscope to a proximal end of the endoscope. By the use of the observation optical system, the necessity to provide an own optical channel for the reflection light can be dispensed with. As a result, the structure of the endoscope is more compact and the endoscope can be produced more easily and cost-efficiently.

Further, it is advantageous when the endoscope has a beam splitter that couples the detection light into the illumination optical system or the detection optical system. It is particularly advantageous when the beam splitter couples the reflection light out of the detection optical system or the observation optical system so that it is incident on a sensor element, in particular a photodetector or a CCD sensor. By the beam splitter, the sensor element and the detection light source can be arranged in a compact manner, as a result whereof an efficient structure of the endoscope is achieved. It is particularly advantageous when the sensor element, the detection light source and the beam splitter are arranged at the distal end of the endoscope, this arrangement is particularly advantageous in the case of so-called chip-on-tip endoscopes, i.e. endoscopes in which an image sensor used for imaging is arranged at the distal end of the endoscope. Further, the beam splitter makes it possible to use the same optical channel for the transport of the detection light and the reflection light so that no additional optical channels have to be provided.

Further, it is advantageous when the endoscope has a sensor element, in particular a photodetector or a CCD chip, which detects the reflection light. The use of a separate sensor element for detection of the reflection light reduces the influence of ambient light on the detection of the reflection light. This increases the reliability with which the reflection light is detected.

Further, it is advantageous when the observation optical system comprises an image sensor which detects both the ambient light entering the distal end of the endoscope shaft and the reflection light. The image sensor can, for example, be arranged at a distal end of the endoscope. The endoscope is then a so-called chip-on-tip endoscope. Alternatively, the image sensor may be arranged in a proximal part of the endoscope, in particular in an endoscope body. Preferably, the endoscope comprises a control unit for further processing data detected by the image sensor.

It is particularly advantageous when the arrangement comprises a control unit which, only in a first operating mode, processes images captured by the image sensor for image display, and which controls the detection light source such that the detection light source emits the detection light only in a second operating mode, wherein in the second operating mode the image sensor detects the reflection light reflected by the light-reflecting element. As a result, it is prevented that disturbing effects during the detection of the endoscope sheath, such as reflexes, are generated in the displayed image or during image processing. For example, the image sensor captures 30 images (frames) per second, of which only 29 are further processed for image display. The image not further processed for image display is used for detection of the reflection light. Alternatively, the image sensor captures 31 images per second, of which one is used for detection of the reflection light. This has the advantage that 30 images per second are further processed for image display and are displayed, which has a very natural and pleasant effect for the human eye.

It is advantageous when the detection light source emits the illumination light and when the detection light is coupled out of the illumination light. By using a single light source for generating the illumination light and the detection light, a particularly compact structure of the endoscope may be achieved.

It is particularly advantageous when the detection light source emits detection light in an ultraviolet (UV), infrared (IR) or near infrared (NIR) wavelength range. As a result, only light with a wavelength range outside the visible light is used as a reflection light. This reduces the influence of ambient light on the detection of the reflection light. As a result, the correct installation of the endoscope sheath on the endoscope can be determined reliably.

Further, it is advantageous when the detection light source emits coherent detection light. In particular, the coherent detection light can be laser light. By using laser light, in particular the distance between the distal end of the endoscope and the optical element can be determined by way of triangulation calculation. This enables a particularly exact determination of the position of the optical element with respect to the endoscope, as a result whereof the correct seat of the endoscope sheath on the endoscope can be determined particularly reliably.

When providing different optical elements in different endoscope sheaths, the imaging of the light detected with the aid of the endoscope can be varied by selecting the endoscope sheath so that the optical image capturing properties of the endoscope may be varied by selecting the sheath.

The endoscope may be a mono-endoscope, i.e. an endoscope with only one optical channel, or a stereoscopic endoscope. The observation optical system of the stereoscopic endoscope has a second optical channel. Alternatively, the stereoscopic endoscope comprises a second observation optical system forming the second optical channel.

Preferably, the detection light source is arranged in the endoscope. The detection light source is, for example, formed by an LED. In particular, the detection light source may be arranged at the distal end of the endoscope. This is particularly advantageous when the endoscope is a chip-on-tip endoscope. Alternatively, the detection light source may be arranged in a proximal part of the endoscope, in particular in an endoscope body.

It is particularly advantageous when the detection light source and the sensor element operate in lock-in technology. For this, the detection light emitted by the detection light source is modulated with a known reference signal. With the aid of a so-called lock-in amplifier, which is arranged downstream of the sensor element, the reflection light may reliably be separated from the background noise on the basis of the known reference signal. Thus, a low signal-to-noise ratio of the arrangement is achieved.

The distance between the optical element and the distal end of the endoscope preferably has a value in the range between 10 μm and 200 μm. This prevents an influence of the ambient light on the detection of the reflection light, as a result whereof a reliable detection of the reflection light is possible.

Further features and advantages of the invention result from the following description which explains the invention in more detail on the basis of embodiments in connection with the enclosed Figures.

DRAWINGS

FIG. 2b shows a schematic illustration of a front view of the stereoscopic endoscope according to the second embodiment of FIG. 2a;

FIG. 2c shows a schematic illustration of an optical element of the sterile endoscope sheath of the stereoscopic endoscope according to the second embodiment of FIG. 2a;

FIG. 3b shows a schematic illustration of a front view of the stereoscopic endoscope according to a third embodiment of FIG. 3a;

FIG. 3c shows a schematic illustration of an optical element of the sterile endoscope sheath of the stereoscopic endoscope according to the third embodiment of FIG. 3a;

FIG. 4a shows a schematic sectional view of an arrangement with a mono-endoscope and a sterile endoscope sheath according to a fourth embodiment;

FIG. 4b shows a schematic illustration of a front view of the mono-endoscope according to the fourth embodiment of FIG. 4a;

FIG. 4c shows a schematic illustration of an optical element of the sterile endoscope sheath of the mono-endoscope according to the fourth embodiment of FIG. 4a;

FIG. 5a shows a schematic sectional view of an arrangement with a stereoscopic endoscope and a sterile endoscope sheath according to a fifth embodiment;

FIG. 5b shows a schematic illustration of a front view of the stereoscopic endoscope according to the fifth embodiment of FIG. 5a;

FIG. 5c shows a schematic illustration of an optical element of the sterile endoscope sheath of the stereoscopic endoscope according to the fifth embodiment of FIG. 5a;

FIG. 6a shows a schematic sectional view of an arrangement with a mono-endoscope and a sterile endoscope sheath according to a sixth embodiment;

FIG. 6b shows a schematic illustration of a front view of the mono-endoscope according to the sixth embodiment of FIG. 6a;

FIG. 6c shows a schematic illustration of an optical element of the sterile endoscope sheath of the mono-endoscope according to the sixth embodiment of FIG. 6a;

DESCRIPTION

Figure 1:
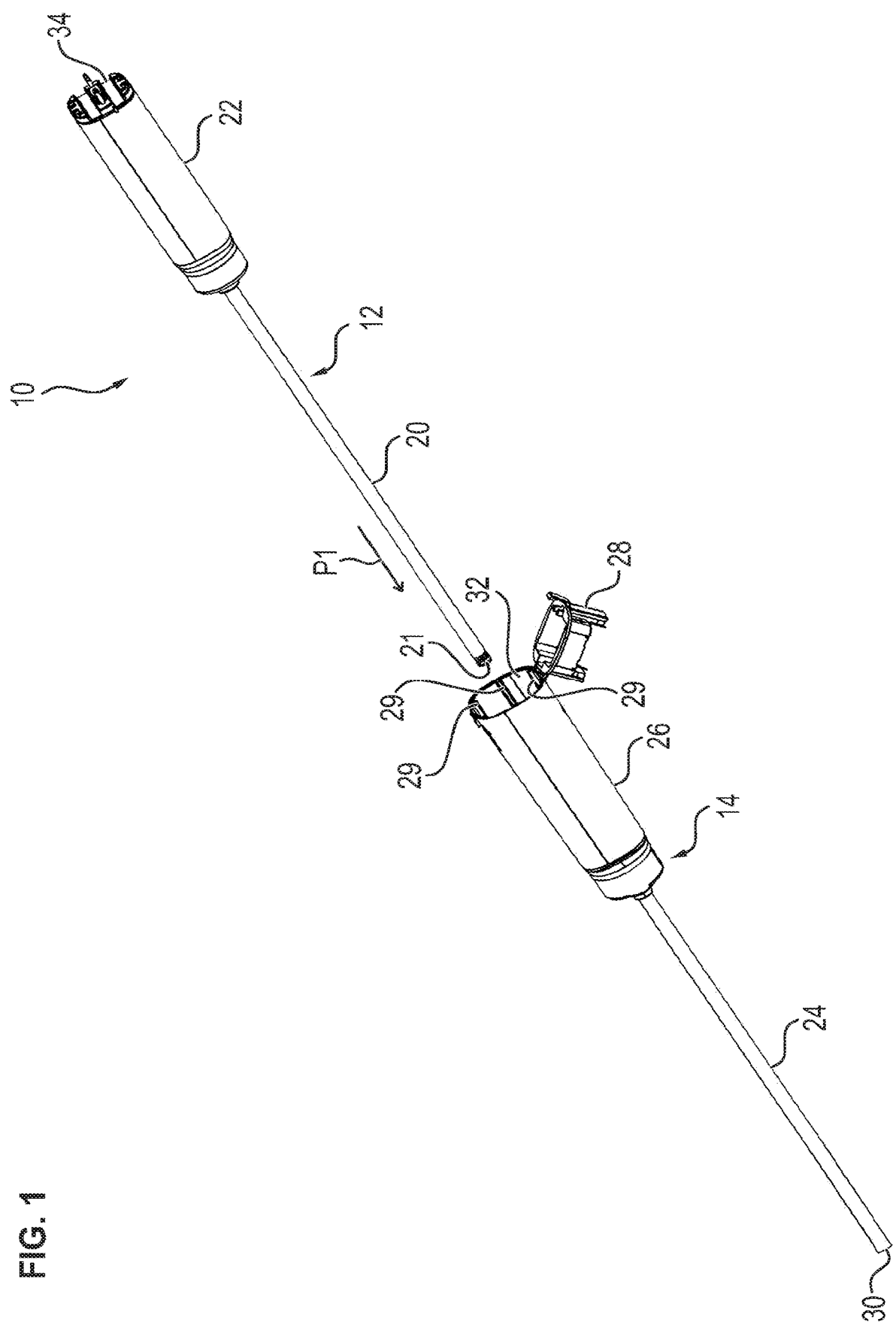
FIG. 1 shows an arrangement for the sterile handling of a non-sterile endoscope in a sterile environment with a sterile endoscope sheath according to a first embodiment.

FIG. 1 shows an arrangement 10 for the sterile handling of a non-sterile endoscope 12 in a sterile environment with a sterile endoscope sheath 14 according to a first embodiment.

The endoscope 12 has an endoscope shaft 20 pointing in a distal direction and an endoscope body 22 arranged at a proximal end of the endoscope shaft 20. The endoscope 12, in particular the inner structure of the endoscope 12, is described in the following in more detail with reference to FIGS. 2a, 2b, 3a, 3b, 4a, 4b, 5a, 5b, 6a, 6b, 7a and 7b.

The endoscope sheath 14 comprises a front part 24 which serves to receive the endoscope shaft 20 that is at least partially insertable into a body of a patient. The front part 24 of the endoscope sheath 14 is closed at the distal end with the aid of an optical element 30 having a light-reflecting element not illustrated in FIG. 1. Specific embodiments of the optical element 30 are described in more detail in the following in connection with FIGS. 2c, 3c, 4c, 5c, 6c and 7c.

The endoscope sheath 14 further comprises a middle part 26 for receiving the endoscope body 22 and a closing element 28 with a sterile lock connected to the middle part 26. By the closing element 28 a feeding and removal opening 32 of the endoscope sheath 14 for inserting and removing an endoscope into and from the endoscope sheath 14, respectively, is formed. With the aid of the sterile lock, a contact area 34 of the endoscope 12 with electric contacts and optical connecting elements is shieldable in a sterile manner.

For receiving the endoscope 12 in the endoscope sheath 14, the endoscope 12 is inserted in the direction of the arrow P1 through the open feeding and removal opening 32 into the endoscope sheath 14. For this, the endoscope shaft 20 is first inserted into the feeding and removal opening 32 and subsequently pushed up into the front part 24 of the endoscope sheath 14 so that a tip 21 of the endoscope shaft 20 is arranged opposite to the optical element 30 of the endoscope sheath 14 arranged at the distal end of the front part 24. When inserting the endoscope body 22 through the feeding and removal opening 32 into the middle part 26 of the endoscope sheath 14, the endoscope body 22 is guided by guiding webs 29 present on the inside in the middle part 26 of the endoscope sheath 14 and held in a predefined position in the middle part 26 of the endoscope sheath 14.

The endoscope sheath 14a comprises a front part 24 which serves to receive the endoscope shaft 20 that is at least partially insertable into a body of a patient. The front part 24 of the endoscope sheath 14a is closed at the distal end with the aid of an optical element 30 having a light-reflecting element not illustrated in FIG. 1. Specific embodiments of the optical element 30 are described in more detail in the following in connection with FIGS. 2c, 3c, 4c, 5c, 6c and 7c.

Figure 2A:
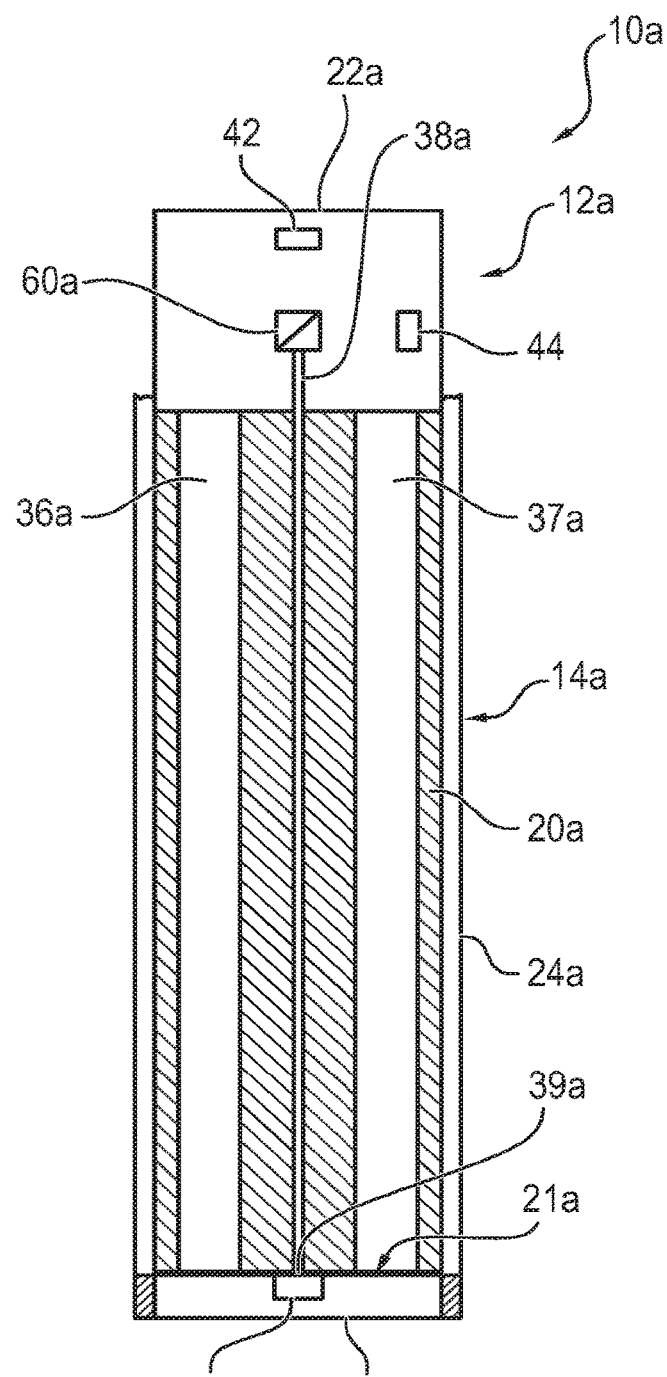
FIG. 2a shows a schematic sectional view of an arrangement with a stereoscopic endoscope having a detection optical system different from an observation optical system, and with a sterile endoscope sheath having an optical element arranged at a distal end, according to a second embodiment.

In FIG. 2a, only a front part 24a of the endoscope sheath 14a is shown. The further structure and the function of the endoscope sheath 14a corresponds to the endoscope sheath 14 according to FIG. 1. The distal end of the front part 24a of the endoscope sheath 14a is closed by an optical element 30a, which is a glass pane. A light-reflecting element 46a is arranged at the proximal side of the optical element 30a. The light-reflecting element 46a is arranged such that it is opposite to a distal end 39a of the detection optical system 38a.

The endoscope 12a has an endoscope shaft 20a extending in distal direction and comprising the detection optical system 38a and the observation optical system 36a, 37a. The endoscope 12a further has an endoscope body 22a arranged at the proximal end of the endoscope shaft 20a, in which body in particular a beam splitter 60a, a detection light source 42 and a sensor element 44 are arranged.

Detection light originating from the detection light source 42 is coupled into the detection optical system 38a by the beam splitter 60a. The detection optical system 38a guides the detection light to a tip 21a arranged at the distal end of the endoscope shaft 20a, where it exits from the distal end 39a of the detection optical system 38a. The exiting detection light is reflected by the light-reflecting element 46a arranged opposite to the distal end 39a of the detection optical system 38a as reflection light toward the detection optical system 38a. The reflection light is guided through the detection optical system 38a from the distal end 39a of the detection optical system 38a to the beam splitter 60a. After the reflection light has passed through the beam splitter 60a, it is incident on the sensor element 44 which detects the reflection light.

The observation optical system 36a, 37a comprises two optical channels. Through the two optical channels, ambient light entering the tip 21a of the endoscope shaft 20a is guided from the tip 21a to the proximal end of the endoscope 12a. As a result, a stereoscopic observation of an area distal to the tip 21a is possible.

Figure 2B:
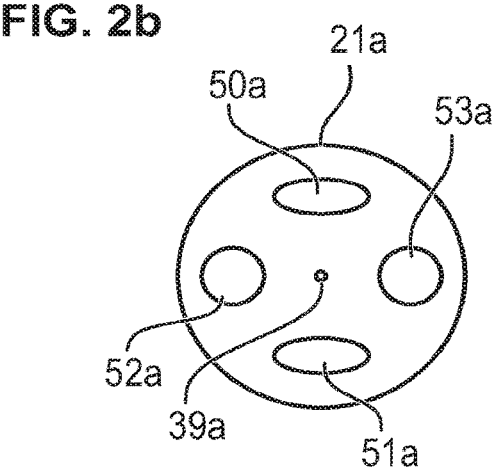

FIG. 2b shows a schematic illustration of a front view of the stereoscopic endoscope 12a according to the second embodiment of FIG. 2a, as viewed from a distal side. The distal end 39a of the detection optical system 38a is arranged centrally. In the illustration of FIG. 2b, to the left and to the right, i.e. on both sides, of the distal end 39a of the detection optical system 38a, one window 52a, 53a of the observation optical system 36a, 37a each is arranged. In the illustration of FIG. 2b, above and below the distal end 39a of the detection optical system 38a one distal end 50a, 51a of a two-channel illumination optical system each is arranged for illuminating the area distal to the tip 21a.

Figure 2C:
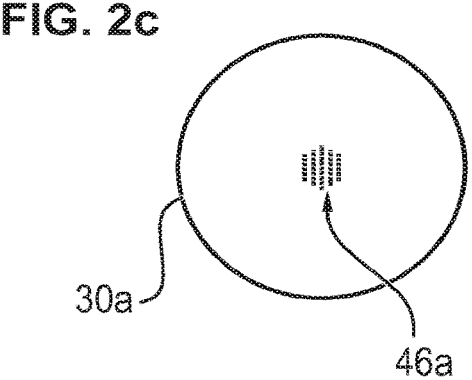

FIG. 2c shows a top view of the optical element 30a of the sterile endoscope sheath 14a of the stereoscopic endoscope 12a according to the second embodiment of FIG. 2a, as viewed from a proximal side. The light-reflecting element 46a is arranged centrally on the optical element 30a and is designed as a light-reflecting coating which has been applied to the optical element 30a.

Figure 3A:
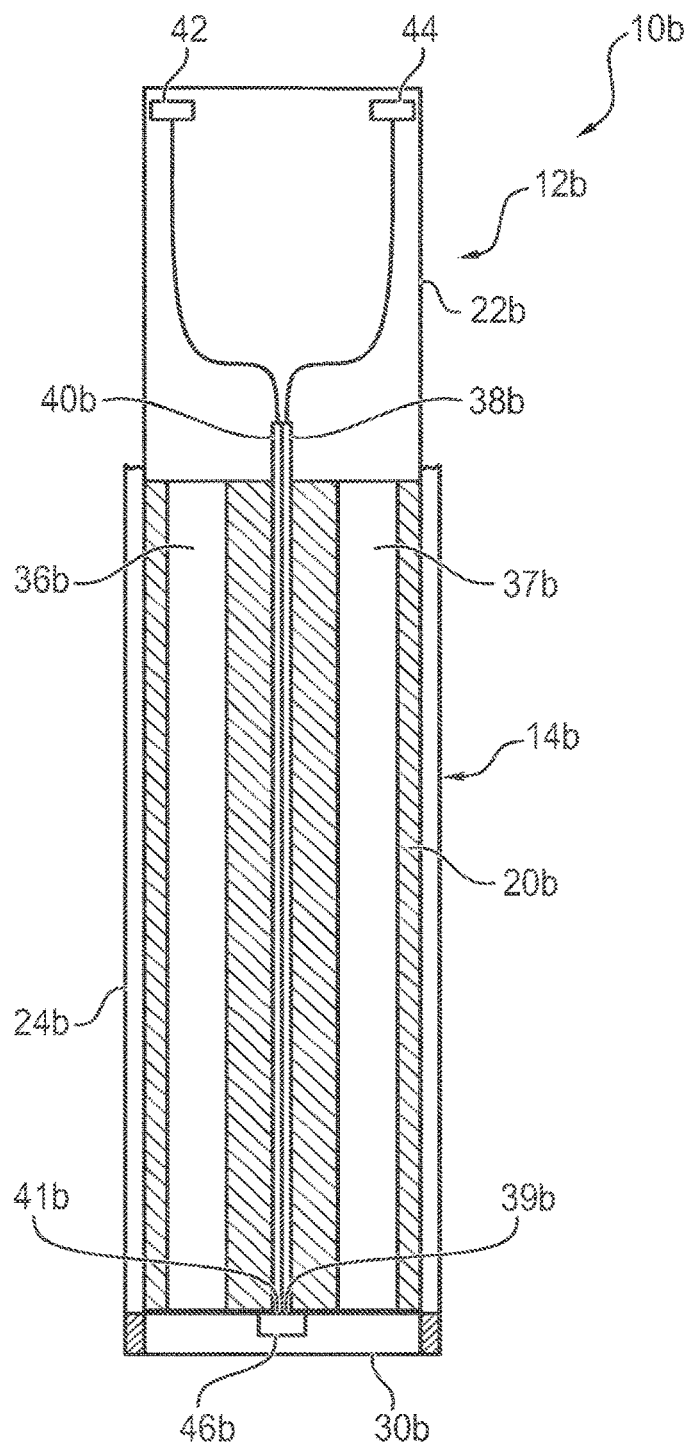
FIG. 3a shows a schematic sectional view of an arrangement with a stereoscopic endoscope and a sterile endoscope sheath according to a third embodiment.

FIG. 3a shows a schematic sectional view of an arrangement 10b according to a third embodiment. The arrangement 10b comprises a stereoscopic endoscope 12b with an endoscope body 22b, which has the detection optical system that is different from the observation optical system 36b, 37b and an optical fiber 40b for guiding detection light. Further, the arrangement 10b comprises a sterile endoscope sheath 14b which has an optical element 30b arranged at the distal end. The arrangement 10b of FIG. 3 differs from the arrangement 10a according to FIGS. 2a to 2c substantially in that the endoscope 12b has the optical fiber 40b for guiding the detection light. The endoscope sheath 24b according to the third embodiment of FIG. 3a and the endoscope sheath 24a according to the second embodiment of FIG. 2a are identically designed.

The detection light emitted by the detection light source 42 is coupled into the optical fiber 40b. The optical fiber 40b guides the detection light to the tip 21b at the distal end of the endoscope shaft 20b, where it exits from a distal end 41b of the optical fiber 40b. The exiting detection light is reflected by the light-reflecting element 46b arranged opposite to the distal end 41b of the optical fiber 40b as reflection light toward the detection optical system 38b. The reflection light is guided through the detection optical system 38b from the distal end 39b of the detection optical system 38b to the sensor element 44 which detects the reflection light. The reflection of the detection light at the tip 21b is still explained in more detail in the following with reference to FIG. 9.

Figure 3B:
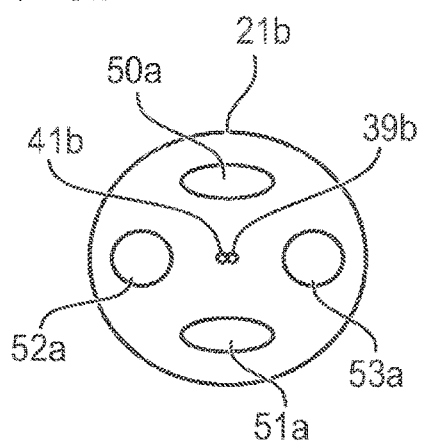

FIG. 3b shows a schematic illustration of a front view of the stereoscopic endoscope 12b according to the third embodiment of FIG. 3a, as viewed from a distal side. The tip 21b of the endoscope 12b according to the third embodiment of FIG. 3a differs from the tip 21a of the endoscope 12a according to the second embodiment of FIG. 2a in that in addition to the distal end 39b of the detection optical system 38b also the distal end 41b of the optical fiber 40b is arranged centrally at the tip 21b.

Figure 3C:
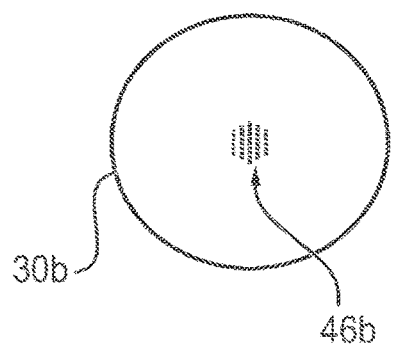

FIG. 3c shows a schematic illustration of the optical element 30b of the sterile endoscope sheath 14b according to the third embodiment of FIGS. 3a and 3b, as viewed from a proximal side. The optical element 30b of the sterile endoscope sheath 14b according to the third embodiment of FIG. 3a is identical to the optical element 30a of the sterile endoscope sheath 14a according to the second embodiment of FIG. 2a.

FIG. 4a shows a schematic sectional view of an arrangement 10c according to a fourth embodiment with a mono-endoscope 12c having an optical fiber 40c for guiding the detection light, and with the sterile endoscope sheath 14c having the optical element 30c arranged at the distal end. The non-sterile mono-endoscope 12c is received in the sterile endoscope sheath 14c and is shielded by it in a sterile manner against the environment.

Only a front part 24c of the endoscope sheath 14c is shown in FIG. 4a. The other structure of the endoscope sheath 14c corresponds to the endoscope sheath 14 according to FIG. 1. The distal end of the front part 24c of the endoscope sheath 14c is closed by an optical element 30c. On the proximal side of the optical element 30c, there is a light-reflecting element 46c. The light-reflecting element 46c is arranged such that it is opposite to a window 52c of the observation optical system 36c.

The endoscope 12c has an endoscope shaft 20c pointing in a distal direction and comprising the optical fiber 40c and the observation optical system 36c which has an optical channel. The endoscope 12c further has an endoscope body 22c arranged at the proximal end of the endoscope shaft 20c, in which body in particular the detection light source 42, an image sensor 54c, a control unit 58c and further optical elements, such as prisms, lenses or diaphragms assigned to the observation optical system 36c and generally identified with the reference sign 56c are arranged.

The detection light emitted by the detection light source 42 is coupled into the optical fiber 40c. The optical fiber 40c guides the detection light to the tip 21c arranged at the distal end of the endoscope shaft 20c, where it exits from a distal end 41c of the optical fiber 40c. The exiting detection light is reflected by the light-reflecting element 46c arranged opposite to the window 52c of the observation optical system 36c as reflection light toward the window 52c of the observation optical system 36c. The reflection light is guided through the observation optical system 36c and the optical elements 56c assigned to the observation optical system 36c up to the image sensor 54c which detects the reflection light.

Only in a first operating mode, the control unit 58c processes images captured by the image sensor 54c for image display. Further, the control unit 58c controls the detection light source 42 such that the detection light source 42 emits the detection light only in a second operating mode. This is explained in more detail further below in connection with FIG. 7.

FIG. 4b shows a schematic illustration of the mono-endoscope 12c according to the fourth embodiment of FIG. 4a, as viewed from a distal side. In the illustration of FIG. 4b, the end of the optical fiber 41c is arranged to the right of the centrally arranged window 52c of the observation optical system 36c. In the illustration of FIG. 4b, one distal end 50c, 51c of an illumination optical system for illuminating the area distal to the tip 21c each is arranged above and below the window 52c.

FIG. 4c shows a schematic illustration of the optical element 30c of the sterile endoscope sheath 14c for the mono-endoscope 12c according to the fourth embodiment of FIG. 4a, as viewed from a proximal side. The light-reflecting element 46c is arranged to the right of a central point 31c, marked with an x in FIG. 4c, on the proximal side, i.e. the inside of the optical element 30a. The light-reflecting element 46c is in the present embodiment designed as a light-reflecting coating which has been applied to the optical element 30c.

FIG. 5a shows a schematic illustration of an arrangement 10d according to a fifth embodiment with a stereoscopic endoscope 12d having two optical fibers 40d, 48d for guiding the detection light. Further, the arrangement 10d comprises a sterile endoscope sheath 14d having an optical element arranged at the distal end. The stereoscopic endoscope 12d is received in the sterile endoscope sheath 14d such that it is shielded against the environment in a sterile manner. The arrangement 10d according to the fifth embodiment of FIG. 5a differs from the arrangement 10c according to the fourth embodiment of FIG. 4a substantially by the second optical fiber 48d.

The endoscope 12d has an endoscope shaft 20d pointing in distal direction and comprising the optical fibers 40d, 48d and an observation optical system 36d, 37d having two optical channels. The endoscope 12d further has an endoscope body 22d arranged at the proximal end of the endoscope shaft 20d, in which body the detection light source 42, a first image sensor 54d, a second image sensor 55d, a control unit 58d and further optical elements, such as prisms, lenses or diaphragms assigned to the observation optical system 36d, 37d and generally identified with the reference sign 56d are arranged.

In FIG. 5a, only a front part 24d of the endoscope sheath 14d is shown. The other structure of the endoscope sheath 14d corresponds to the endoscope sheath 14 according to FIG. 1. A distal end of the front part 24d of the endoscope sheath 14d is closed by an optical element 30d. At the proximal side of the optical element 30d, a first light-reflecting element 46d and a second light-reflecting element 47d are arranged. The first light-reflecting element 46d is arranged such that it is opposite to a first window 52d of the observation optical system 36d, 37d. The second light-reflecting element 47d is arranged such that it is opposite to a second window 53d of the observation optical system 36d, 37d.

The detection light emitted by the detection light source 42 is coupled into the first optical fiber 40d. The first optical fiber 40d guides the detection light to the tip 21d arranged at the distal end of the endoscope shaft 20d, at which tip it exits from a distal end 41d of the first optical fiber 40d. The exiting detection light is reflected by the first light-reflecting element 46d arranged opposite to the first window 52d of the observation optical system 36d as reflection light toward the first window 52d of the observation optical system 36d. The reflection light is guided through the observation optical system 36d and the optical elements 56d assigned to the observation optical system 36d up to the first image sensor 54d which detects the reflection light.

The detection light originating from the detection light source 42 is further coupled into the second optical fiber 48d. The second optical fiber 48d guides the detection light to the tip 21d arranged at the distal end of the endoscope shaft 20d, at which tip it exits from a distal end 49d of the second optical fiber 48d. The exiting detection light is reflected by the second light-reflecting element 47d arranged opposite to the second window 53d of the observation optical system 37d as reflection light toward the second window 53d of the observation optical system 37d. The reflection light is guided through the observation optical system 37d and the optical elements 56d assigned to the observation optical system 37d up to the second image sensor 55d that detects the reflection light.

Only in a first operating mode, the control unit 58d processes images captured by the first and the second image sensor 54d, 55d for image display. The further processed images can be output via an output unit, for example, a screen. Further, the control unit 58d controls the detection light source 42 such that the detection light source 42 emits the detection light only in a second operating mode. In the second operating mode, the images captured by the first and second image sensor 54d, 55d are not processed further for image display. The control unit 58d determines in the second operating mode an intensity of the reflection light from the images captured by the first and the second image sensor 54d, 55d. If this intensity is below a preset threshold value, this is an indication of an incorrect seat of the endoscope sheath 14d on the endoscope 12d. In the second operating mode, the output unit can output the last image captured by the first and the second image sensor 54d, 55d, respectively, in the first operating mode.

FIG. 5b shows a schematic illustration of a front view of the stereoscopic endoscope 12d according to the fifth embodiment of FIG. 5a, as viewed from a distal side. In the illustration of FIG. 5b, the distal ends 41d, 49d of the two optical fibers 40d, 48d are arranged to the left and to the right of the first and the second window 52d, 53d, respectively, of the observation optical system 36d, 37d. In the illustration of FIG. 5b, one distal end 50d, 51d of an illumination optical system for illuminating the area distal to the tip 21d each is arranged above and below the first and the second window 52d, 53d.

FIG. 5c shows a schematic illustration of the optical element 30d of the sterile endoscope sheath 14d according to the fifth embodiment of FIG. 5a, as viewed from a proximal side. The first light-reflecting element 46d is arranged to the left of a centrally arranged point 31d, which is marked with an x in FIG. 5c, on the optical element 30d. The second light-reflecting element 47d is arranged to the right of the centrally arranged point 31d on the optical element 30d. The first and the second light-reflecting element 46d, 47d are formed in the present embodiment as light-reflecting coatings which have been applied to the optical element 30d.

FIG. 6a shows a schematic sectional view of an arrangement 10e according to a sixth embodiment. The arrangement 10e comprises a mono-endoscope 12e consisting of an endoscope body 22e and an endoscope shaft 20e and having a beam splitter 60e for coupling in the detection light. Further, the arrangement 10e has a sterile endoscope sheath 14e having an optical element arranged at the distal end. The non-sterile mono-endoscope 12e is received in the endoscope sheath 14e and is thus shielded against the environment in a sterile manner. The arrangement 10e according to the sixth embodiment of FIG. 6a differs from the arrangement 10c according to the fifth embodiment of FIG. 5 substantially in that the detection light is coupled into an observation optical system 36e of the mono-endoscope 12e by the beam splitter 60e.

The detection light originating from the detection light source 42 is coupled into the observation optical system 36e with the aid of the beam splitter 60e. The observation optical system 36e guides the detection light to the tip 21e arranged at the distal end of the endoscope shaft 20e, at which tip it exits from a window 52e of an observation optical system 36e. The exiting detection light is reflected by the light-reflecting element 46e arranged opposite to the window 52e of the observation optical system 36e as reflection light toward the window 52e. The reflection light is guided through the observation optical system 36e and the optical elements 56e assigned to the observation optical system 36e up to the image sensor 54e which detects the reflection light.

Only in a first operating mode, the control unit 58e processes images captured by the image sensor 54e for image display. Further, the control unit 58e controls the detection light source 42 such that the detection light source 42 emits the detection light only in a second operating mode. In the second operating mode, the images captured by the image sensor 54e are not further processed for image display. The control unit 58e determines in the second operating mode an intensity of the reflection light from the images captured by the image sensor 54e. If this intensity is below a preset threshold value, this is an indication of an incorrect seat of the endoscope sheath 14e on the endoscope 12e. In the second operating mode, the output unit can output the last image captured by the image sensor 54e in the first operating mode.

FIG. 6b shows a schematic illustration of the non-sterile mono-endoscope 12e according to the sixth embodiment of FIG. 6a, as viewed from a distal side. The tip 21e of the endoscope 12e according to FIG. 6a differs from the tip 21c of the endoscope 12c according to FIG. 4a in that the tip 21e of the endoscope 12e according to FIG. 6a does not have a distal end of an optical fiber since the reflection light is guided through the observation optical system 36e and the optical elements 56e assigned to the observation optical system 36e. In the illustration of FIG. 6b, one distal end 50d, 51d of an illumination optical system for illuminating the area distal to the tip 21d each is arranged above and below the window 52e.

FIG. 6c shows a schematic illustration of the optical element 30e of the sterile endoscope sheath 14e according to the sixth embodiment of FIG. 6a, as viewed from a proximal side. The optical element 30e of the sterile endoscope sheath 14e according to the sixth embodiment of FIG. 6a is identical to the optical element 30a of the sterile endoscope sheath 14a according to the second embodiment of FIG. 2a.

Figure 7:
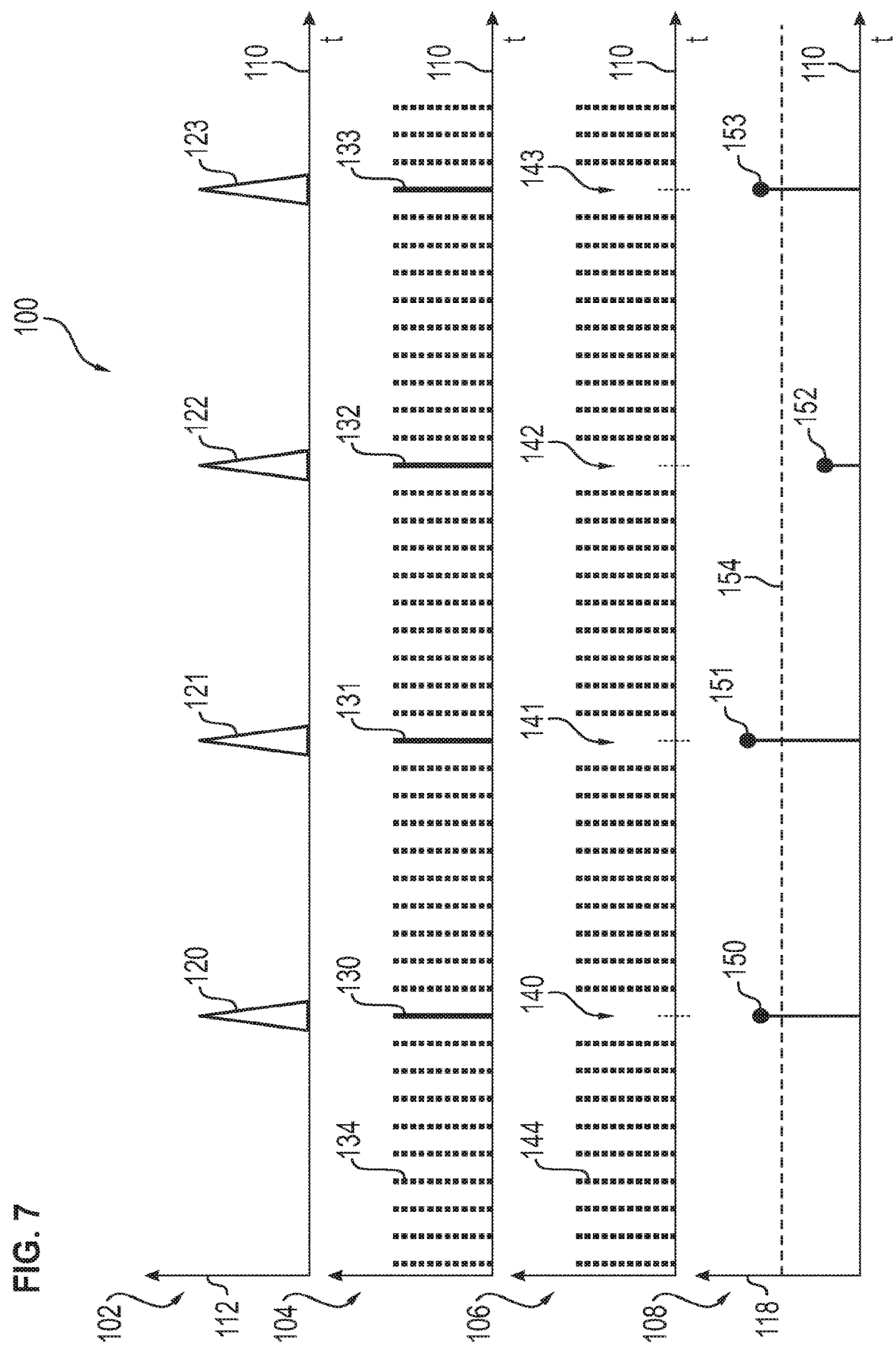
FIG. 7 shows a diagram for explaining the functioning of the arrangement for the sterile handling of a non-sterile endoscope according to the fourth embodiment of FIGS. 4a to 4c.

FIG. 7 shows a diagram 100 for explaining the functioning of the arrangement 10c for the sterile handling of a non-sterile endoscope according to the fourth embodiment of FIGS. 4a to 4c. The diagram 100 comprises four sub-diagrams 102, 104, 106, 108. The four sub-diagrams 102, 104, 106, 108 each have a time axis 110, which indicates from left to right a time course.

The first sub-diagram 102 has an ordinate axis 112 which indicates the intensity of the illumination light emitted by the detection light source 42 in the first operating mode. As an example, a regular sequence of four detection light pulses 120, 121, 122, 123 is shown.

The second sub-diagram 104 indicates at which points in time the image sensor 54c either detects the detection light and the ambient light or only the ambient light. Points in time at which the image sensor 54c detects the detection light and the ambient light are illustrated as pulses 130, 131, 132, 133 in the second sub-diagram 104. These points in time correspond to points in time at which the detection light source 42 emits the detection light pulses 120, 121, 122, 123. Points in time at which the image sensor 54c only detects the ambient light are illustrated as dotted pulses in the second sub-diagram 104, of which exemplarily one pulse is identified with the reference sign 134. These points in time correspond to the points in time at which the detection light source 42 emits no detection light.

The third sub-diagram 106 indicates at which points in time the control unit 58c further processes the images captured by the image sensor 54c in the second operating mode for image display. These points in time are illustrated as pulses in the third sub-diagram 106, of which exemplarily one pulse is identified with the reference sign 144. At the points in time at which the image sensor 54c detects the detection light and the ambient light, the control unit 58c does not forward the image captured by the image sensor 54c for image display but determines an intensity of the reflection light from the images captured by the image sensor 54c. If this intensity is below a preset threshold value, this is an indication of an incorrect seat of the endoscope sheath 14c on the endoscope 12c. In the second operating mode, the output unit can output the last image captured by the image sensor 54c in the first operating mode. These points in time are identified in the third sub-diagram 106 with the reference signs 140, 141, 142, 143.

The fourth sub-diagram 108 has an ordinate axis 118 which indicates the intensity of the illumination light detected by the image sensor 54c, which intensity is determined by the control unit 58c. In the fourth sub-diagram 108, four intensity values 150, 151, 152, 153 are shown, which are assigned to the detection light pulses 120, 121, 122, 123. The fourth sub-diagram 108 further shows a horizontal broken line 154 indicating the preset threshold value of the determined intensity of the detection light detected by the image sensor 54c. The first two intensity values 150, 151 as viewed from left and the last intensity value 153 are above the threshold value. The third intensity value 152 as viewed from left is below the threshold value, this indicating an incorrect seat of the endoscope sheath 14c.

The method described in connection with the arrangement 10c of FIG. 4 may alternatively also be performed with the arrangement 10d or 10e according to FIG. 5 or 6.

Figure 8:
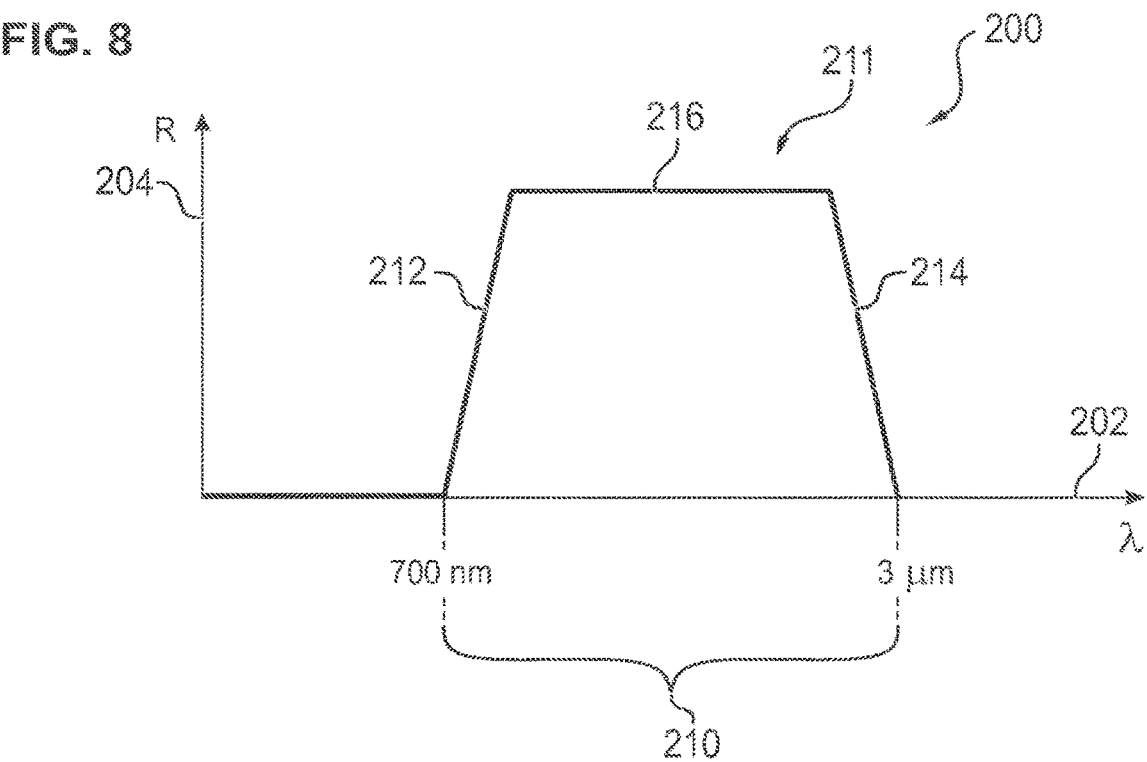
FIG. 8 shows a diagram of a wavelength range of detection light of the arrangement for the sterile handling of a non-sterile endoscope according to the first embodiment of FIG. 1.

FIG. 8 shows a diagram 200 of a wavelength range 210 of the detection light of the arrangement 10 for the sterile handling of a non-sterile endoscope 12 according to the first embodiment of FIG. 1. The wavelength range 210 is only illustrated exemplarily for the arrangement 10 of FIG. 1. In other embodiments, the wavelength range may be different.

The diagram 200 has an abscissa axis 202 on which the wavelength λ is indicated and an ordinate axis 204 indicating an intensity R. The wavelength range 210 is shown as an intensity curve 211. The intensity curve 211 has a first edge 212 at a wavelength λ of 700 nm, i.e. the intensity R of the detection light increases as from a wavelength λ of 700 nm. The intensity curve 211 further has a second edge 214 at a wavelength λ of 3 μm, i.e. the intensity R of the detection light decreases up to a wavelength λ of 3 μm. Between the first and the second edge 212, 214 the intensity distribution 211 has a plateau 216. The wavelength range 210 of the detection light comprises thus wavelengths λ from 700 nm to 3 μm, which corresponds to near infrared light. Alternatively, the detection light may also be ultraviolet light, i.e. the detection light comprises wavelengths λ between 280 nm and 400 nm, or infrared light, i.e. the detection light comprises wavelengths λ between 800 nm and 1 mm.

Figure 9:
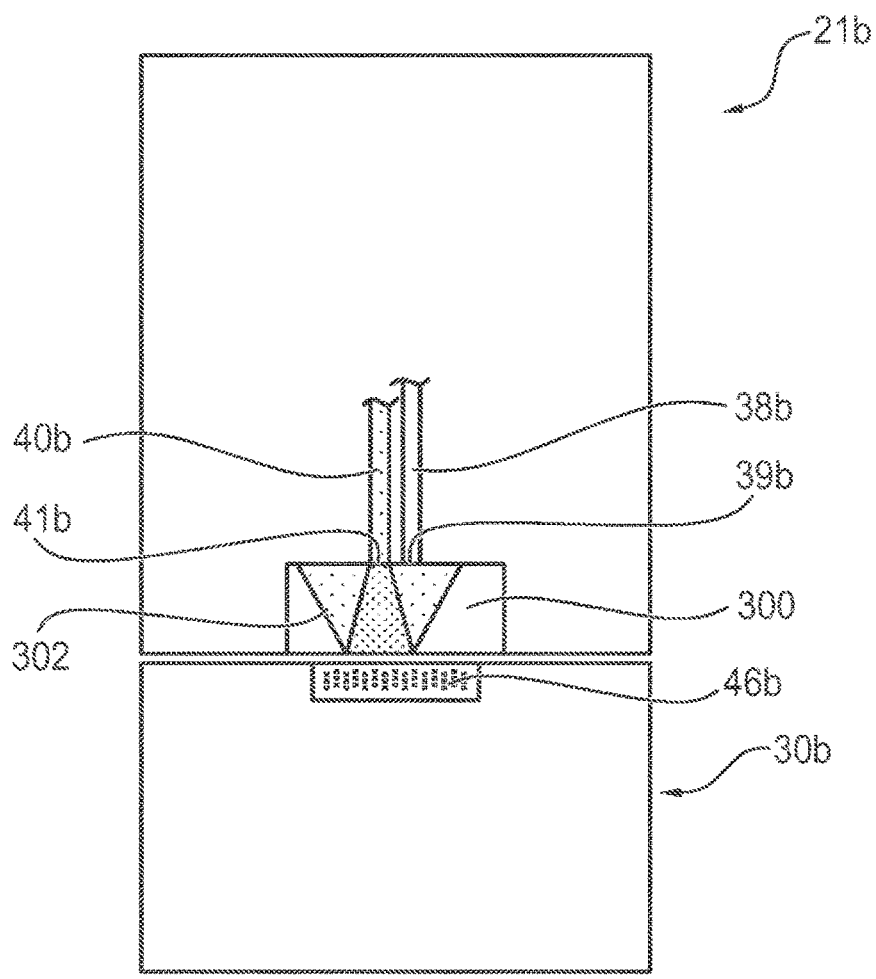
FIG. 9 shows a schematic sectional view of the distal end of the endoscope according to a third embodiment of FIGS. 3a to 3c.

FIG. 9 shows a distal end 21b of the endoscope 12b according to the third embodiment of FIGS. 3a to 3c in a schematic sectional view. The distal end 21b of the endoscope 12b has the distal end 39b of the detection optical system 38b and a distal end 41b of an optical fiber 40b. The distal end 39b of the detection optical system 38b and the distal end 41b of the optical fiber 40b are arranged within a recess 300. Detection light 302 exiting from the distal end 41b of the optical fiber 40b is reflected by the light-reflecting element 46b arranged opposite to the recess 300 on the optical element 30b toward the distal end 39b of the detection optical system 38b. The distance between the distal end 41b of the optical fiber 40b and the light-reflecting element 46b is increased by the recess 300 so that the light bundle of the exiting detection light 302 is made larger. Alternatively or additionally, the numerical aperture of the optical fiber 40b may be adapted to achieve a broadening of the light bundle.

The invention claimed is:

1. An arrangement for sterile handling of a non-sterile endoscope in a sterile environment, comprising: a sterile endoscope sheath having an optical element arranged at a distal end of the endoscope sheath wherein the optical element has one of a light-reflecting element or a light-reflecting area which reflects detection light emitted from a detection light source as reflection light toward a proximal end of the sterile endoscope sheath, and a non-sterile endoscope comprising an endoscope shaft, an illumination optical system for guiding illumination light and an observation optical system for one of detecting or forwarding ambient light entering a distal end of the endoscope shaft, wherein the non-sterile endoscope is received in the endoscope sheath and is shielded by it in a sterile manner against the environment, wherein the non-sterile endoscope has a detection optical system for guiding the detection light emitted by the detection light source, which the detection optical system is different from the illumination optical system and the observation optical system, wherein the non-sterile endoscope has a beam splitter which couples the detection light into the detection optical system, and wherein the beam splitter couples the reflection light out of the detection optical system so that it is incident on a sensor element, wherein the sensor element is one of a photodetector or a CCD sensor.

2. The arrangement according to claim 1, wherein the one of the light-reflecting element or the light-reflecting area is transparent in at least one optical wavelength range outside a wavelength range of the detection light.

3. The arrangement according to claim 1, wherein the one of the light-reflecting element or the light-reflecting area reflects light in an ultraviolet (UV), an infrared (IR) or a near-infrared (NIR) wavelength range.

4. The arrangement according to claim 1, wherein the one of the light-reflecting element or the light-reflecting area is arranged on a side of the optical element facing the proximal end of the endoscope sheath.

5. The arrangement according to claim 1, wherein the observation optical system guides the reflection light.

6. The arrangement according to claim 1, wherein the detection light source emits the illumination light and the detection light is coupled to the illumination light.

7. The arrangement according to claim 1, wherein the detection light source emits detection light in an ultraviolet, infrared, or near-infrared wavelength range.

8. The arrangement according to claim 1, wherein the detection light source emits coherent detection light.

* * * * *